(12) United States Patent
Wand

(10) Patent No.: US 9,778,335 B2
(45) Date of Patent: Oct. 3, 2017

(54) ENHANCED NUCLEAR SPIN POLARIZATION

(71) Applicant: The Trustees of The University of Pennsylvania, Philadelphia, PA (US)

(72) Inventor: Andrew Joshua Wand, Glen Mills, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/400,471

(22) PCT Filed: May 9, 2013

(86) PCT No.: PCT/US2013/040304
§ 371 (c)(1),
(2) Date: Nov. 11, 2014

(87) PCT Pub. No.: WO2013/169999
PCT Pub. Date: Nov. 14, 2013

(65) Prior Publication Data
US 2015/0130096 A1    May 14, 2015

Related U.S. Application Data

(60) Provisional application No. 61/645,965, filed on May 11, 2012.

(51) Int. Cl.
*G01R 33/465* (2006.01)
*G01R 33/28* (2006.01)
*G01N 24/12* (2006.01)
*G01R 33/44* (2006.01)
*G01R 33/62* (2006.01)

(52) U.S. Cl.
CPC ........... *G01R 33/465* (2013.01); *G01N 24/12* (2013.01); *G01R 33/282* (2013.01); *G01R 33/445* (2013.01); *G01R 33/62* (2013.01)

(58) Field of Classification Search
None
See application file for complete search history.

(56) References Cited

U.S. PATENT DOCUMENTS

| | | | |
|---|---|---|---|
| 6,198,281 B1 | 3/2001 | Wand et al. | |
| 6,486,672 B1 | 11/2002 | Wand et al. | |
| 2009/0121712 A1* | 5/2009 | Han | G01R 33/282 324/307 |
| 2012/0263793 A1* | 10/2012 | Vitaliano | G01N 21/554 424/490 |

FOREIGN PATENT DOCUMENTS

WO    WO 2009/036741 A1    3/2009

OTHER PUBLICATIONS

Yang et al.; "Dielectric Model and Theoretical Analysis of Cationic Reverse Micellar Solutions in CTAB/Isooctane/n-Hexanol/Water Systems"; Langmuir, American Chemical Society; 2007; vol. 23; p. 8732-8739.

(Continued)

*Primary Examiner* — Jeffrey Washville
(74) *Attorney, Agent, or Firm* — Baker & Hostetler LLP

(57) ABSTRACT

The polarization of nuclear spins of a material may be enhanced by encapsulating the material within a reverse micelle.

15 Claims, 17 Drawing Sheets

(56) References Cited

OTHER PUBLICATIONS

Abragam et al.; "Principles of Dynamic Nuclear Polarisation"; Rep. Prog. Phys.; 1978; vol. 41; 1978; p. 395-467.
Gabriel et al.; Dielectric parameters relevant to microwave dielectric heating; Chemical Society Reveiws; 1998; vol. 27 Issue 3; p. 213-223.
Slichter; "The discovery and demonstration of dynamic nuclear polarization—a personal and historical account"; Physical Chemistry Chemical Physics; 2010; vol. 12 Issue 22; p. 5741-5751.
Kielec et al.; "Reverse Micelles in Integral Membrane Protein Structural Biology by Solution NMR Spectroscopy"; Structure; Mar. 2009; vol. 17 Issue 3; p. 345-351.
Valentine et al.; "Reverse Micelle Encapsulation of Membrane-Anchored Proteins for Solution NMR Studies"; Structure; Jan. 2010; vol. 18 Issue 1; p. 9-16.
Peterson et al.; "Forced folding and structural analysis of metastable proteins"; Journal of the American Chemical Society; 2004; vol. 126; p. 9498-9499.
Nucci et al.; "Site-resolved measurement of water-protein interactions by solution NMR"; Nature Structural & Molecular Biolollgy; Feb. 2011; vol. 18 No. 2; p. 245-249.
Babu et al.; "Direct access to the cooperative substructure of proteins and the protein ensemble via cold denaturation"; Nature Structural & Molecular Biology; Apr. 2004; vol. 11 No. 4; p. 352-357.
Redfield; Shuttling device for high-resolution measurements of relaxation and related phenomena in solution at low field, using a shared commercial 500 MHz NMR instrument; Magnetic Resonance in Chemistry; Oct. 2003; vol. 41 Issue 10; p. 753-768.
International Patent Application No. PCT/US2013/040304; Int'l Search Report and the Written Opinion; dated Oct. 25, 2013; 9 pages.
Peterson et al.; "High Resolution NMR Studies of Encapsulated Proteins in Liquid Ethane"; Journal of the American Chemical Society; 2005; vol. 127 No. 29.; p. 10176-10177.
Luisi et al.; "Reverse Micelles as Hosts for Proteins and Small Molecules"; Biochimica et Biophysica Acta; 1988; vol. 947; p. 209-246.
Sezer; "Computation of DNP coupling factors of a nitroxide radical in toluene: seamless combination of MD simulations and analytical calculations"; PCCP; 2012I 15 pages.
Wand et al.; "High-resolution NMR of encapsulated proteins dissolved in low-viscosity fluids"; Proc. Nat'l. Acad. Sci. USA; vol. 95; Dec. 1998; p. 15299-15302.
Griffin et al.; "High field dynamic nuclear polarization—the renaissance"; Physical Chemistry Chemical Physics; vol. 12 No. 22; 2010; p. 5737-5740.
European Patent Application No. 13787639.7; Extended Search Report; dated Jun. 8, 2016; 8 pages.

* cited by examiner

ENHANCED NUCLEAR SPIN POLARIZATION

CROSS-REFERENCE TO RELATED APPLICATIONS

This application is the National Stage of International Application No. PCT/US2013/040304, filed May 9, 2013, which claims the benefit of U.S. Provisional Application No. 61/645,965, filed May 11, 2012, the entireties of which are incorporated herein by reference for any and all purposes.

STATEMENT OF FEDERALLY SPONSORED RESEARCH

This invention was made with government support under grant number MCB1158038 awarded by the National Science Foundation. The government has certain rights in the invention.

TECHNICAL FIELD

The technical field generally relates to nuclear magnetic resonance and dynamic nuclear polarization, and more specifically relates to applications of nuclear magnetic resonance and dynamic nuclear polarization utilizing solutions of reverse micelles.

BACKGROUND

Solution nuclear magnetic resonance (NMR) spectroscopy may be applicable to studies in structural biology and molecular biophysics. However, detection sensitivity of solution NMR is relatively poor.

SUMMARY

The following presents a simplified summary that describes some aspects or embodiments of the subject disclosure. This summary is not an extensive overview of the disclosure. Indeed, additional or alternative embodiments of the subject disclosure may be available beyond those described in the summary.

Reverse micelles may be used in association with nuclear magnetic resonance (NMR) to determine characteristics of a material. Utilization of reverse micelles as described herein may improve detection sensitivity as compared to configurations in which reverse micelles are not used. In various example embodiments, dynamic nuclear polarization (DNP) may be utilized in conjunction with NMR. DNP utilizes cross relaxation between electron spins and nuclear spins to effectuate the polarization of the nuclear spins.

For example, a hydrated material (e.g., a biomaterial) may be encapsulated within a reverse micelle. The reverse micelle may contain a spin radical (e.g., nitroxide radical) and a water core. The water core may comprise water or any appropriate aqueous solution. The reverse micelle may be dissolved in a low dielectric loss solvent (e.g., ethane, propane, butane, etc.). The reverse micelle and solvent solution may be exposed to a magnetic field. Concurrently, the solution may be exposed to electromagnetic radiation. The electromagnetic radiation may have a frequency that causes absorption by the radical resulting in (partial) saturation of the electronic transition. Exposure of the solution to the combined magnetic field and the electromagnetic radiation may cause nonequilibrium polarization of the spin radical. The nonequilibrium polarization of the spin radical, via DNP, may result in transference of polarization to nuclear spins within the surrounding material. And nuclear spin transitions of the polarized material may result in enhanced detection performance for determining characteristic of the material.

BRIEF DESCRIPTION OF THE DRAWINGS

Reference is made here to the accompanying drawings, which are not necessarily drawn to scale.

FIG. 14A, FIG. 14B, and FIG. 14C, illustrates that paramagnetic relaxation effects can be optimized for spin labeled macromolecules encapsulated within a reverse micelle.

DETAILED DESCRIPTION OF ILLUSTRATIVE EMBODIMENTS

Figure 1:
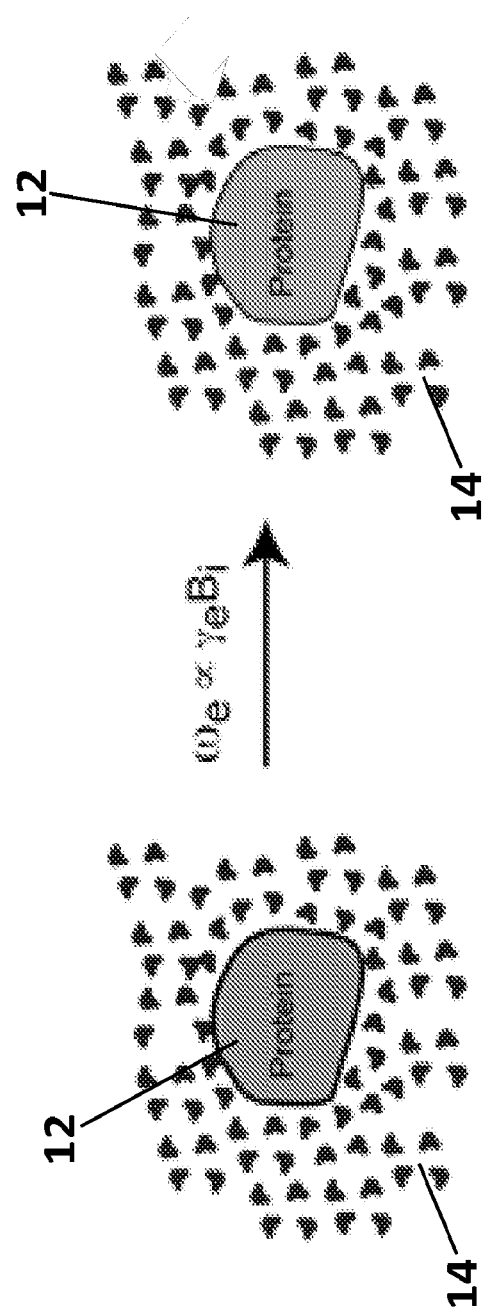
FIG. 1 depicts a solution comprising a protein in water or any appropriate aqueous solution.

Aspects of the instant disclosure are described more fully herein with reference to the accompanying drawings, in which example embodiments are shown. In the following description, for purposes of explanation, numerous specific details are set forth in order to provide an understanding of the various embodiments. However, the instant disclosure may be embodied in many different forms and should not be construed as limited to the example embodiments set forth herein. Like numbers refer to like elements throughout.

NMR comprises inherent insensitivities. Dynamic nuclear polarization (DNP) may offer improvement in this respect. Dynamic nuclear polarization (DNP) uses cross relaxation between electron and nuclear spins to enhance the polarization of nuclear spins. One way to achieve DNP is via cross relaxation by polarized electron spin of neighboring nuclear spins (i.e., the Overhauser effect). The electron transitions of suitable radicals may lie in the GHz spectrum where bulk water or any appropriate aqueous solution absorbs strongly often resulting in catastrophic heating. As described herein however, encapsulating the protein in a water core or any appropriate aqueous solution of a reverse micelle, in combination with DNP, may increase signal strength (potentially up to approximately 660 fold). This may be due to most of the water in the aqueous sample being absent in the reverse micelle sample and the heat generated by irradiation of the remaining water is efficiently dissipated to the organic solvent. In addition, the remaining water or appropriate aqueous solution, which forms the core of the reverse micelle, may be qualitatively different and absorb microwaves at longer wavelengths of EM spectrum.

Utilization of DNP may incorporate saturation of the electronic transition of a stable radical and transfer this non-equilibrium polarization to the hydrogen spins of water, which will in turn transfer polarization to the hydrogens of the macromolecule. For example, the residence times of water on the surface of the protein in bulk solution may be generally too short for efficient transfer of polarization from water to the molecule of ultimate interest. As described herein, in exemplary embodiments, the properties of solutions of encapsulated proteins dissolved in low viscosity solvents are utilized to implement DNP in liquids. Since such samples may be largely transparent to the GHz frequencies, heating during saturation of the electronic transition may be avoided and/or mitigated. In other exemplary embodiments, material such as, for example, nitroxide radicals, may be introduced into the reverse micelle system. In various example embodiments, radicals may be introduced by attaching the radical to the protein, embedding the racial in the reverse micelle shell, introducing free radicals in the aqueous core, or any appropriate combination thereof. Enhancements of the water resonance ranging up to −35 at 0.35 T was observed during experiments of the exemplary embodiment. In the exemplary embodiment, the hydration properties of encapsulated proteins were also found to allow for efficient polarization transfer from water to the protein. These and other observations in the exemplary embodiments suggest that the merging of the reverse micelle encapsulation technology with DNP offers a route to an increase in the sensitivity of materials such as solution NMR spectroscopy of proteins, other bio-molecules, or the like.

The use of DNP to enhance a NMR signal of an NMR solution may be encumbered because solvents such as hydrocarbons (i.e., ethane, propane, butane, or the like) may denature the solution NMR material which may result in loss of structure. The NMR solution may be a protein, polysaccharide, polypeptide, polynucleotide or any appropriate combination thereof.

Figure 2:
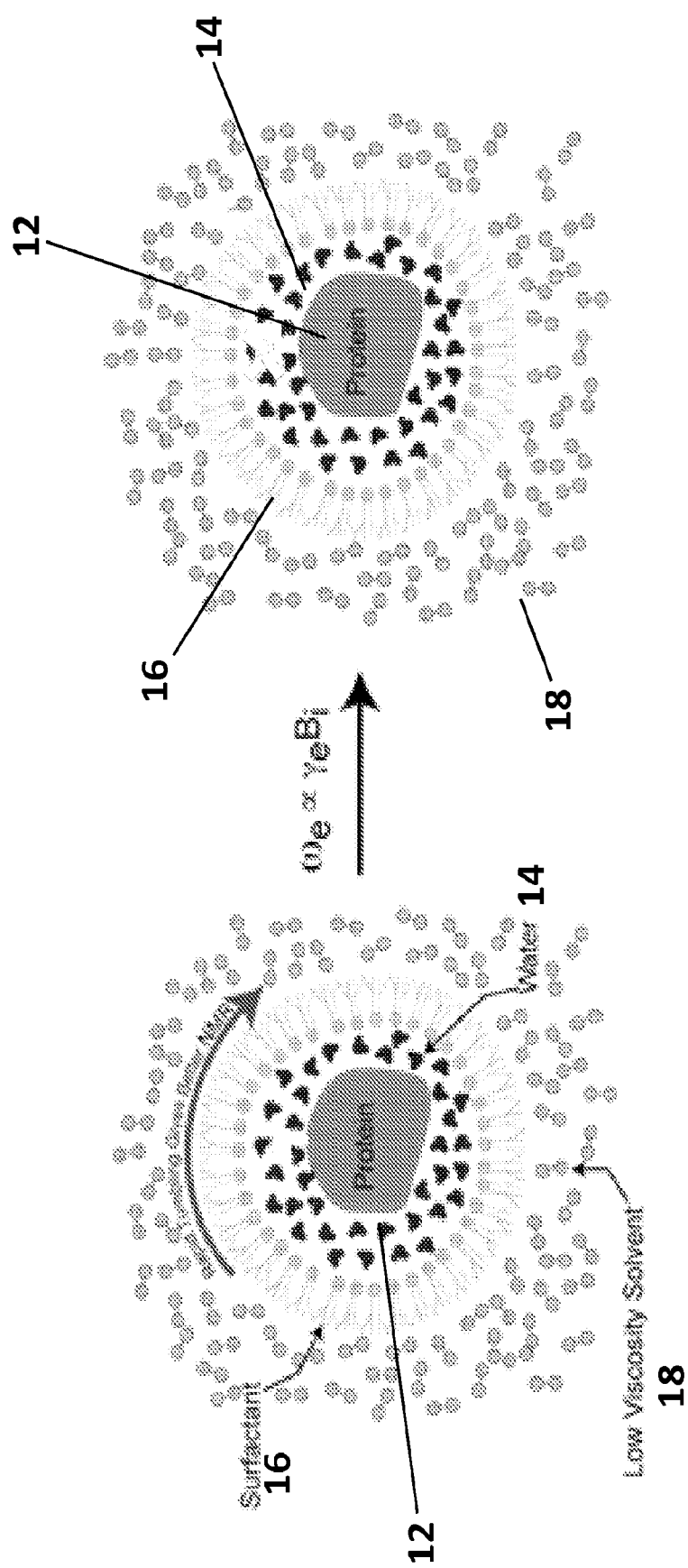
FIG. 2 depicts a solution in which a protein is encapsulated in a reverse micelle.

FIG. 1 depicts a solution comprising a protein 12 in water 14. As saturation of electron transition occurs, depicted by the arrow labeled $\omega_e \propto \gamma_e B_i$. excess heat may destroy the sample protein 12. The frequency of irradiation ($\omega_e$) will be proportional to the applied magnetic field strength. FIG. 2 depicts a solution in which a protein 12 is encapsulated in a reverse micelle. The depictions in FIG. 2 comprise a protein 12, water 14, a surfactant 16, and a solvent 18. The surfactant(s) 16 and water 14 form a reverse micelle. As depicted in FIG. 2, saturation of electron transition, depicted by the arrow labeled $\omega_e \propto \gamma_e B_i$. occurs without excess heat being generated, thus preserving the sample protein 12. Encapsulation of the materials such as solution NMR within a reverse micelle may result in greater than ~98% less water. Encapsulation of the materials such as solution NMR within a reverse micelle may result in water molecules remaining within the core of the reverse micelle being qualitatively different with respect to their motion and time of interaction with an encapsulated molecule.

The structural and dynamic aspects of proteins forms the basis for the understanding of the chemical basis of their functions. Nuclear magnetic resonance in solution has contributed y to this view and the information inherent in the NMR phenomena offers more. Yet, despite tremendous advances in technology, experimental design and analytical strategies, solution NMR spectroscopy of macromolecules remains fundamentally restricted due to its extraordinary insensitivity. Though state-of-the-art multinuclear multidimensional NMR experiments may be routinely carried out on samples in the ~0.5 mM (5 moles per cubic millimeter) concentration range, many systems and problems of interest remain inaccessible due to limited solubility and/or limited availability. This is true for materials such as biopolymers, specifically proteins and nucleic acids or the like. Thus, a further extension of the sensitivity of the NMR method well into the low μM ($10^{-3}$ moles per cubic millimeter) concentration regime would be useful.

In an exemplary embodiment to increase the sensitivity of NMR, nuclear spins are coupled to a reservoir with much higher polarization, such as unpaired electrons. Dynamic nuclear polarization (DNP) may be understood to be based on the transfer of the large electron spin polarization to nuclear spins ($\gamma_e/\gamma_n$ ~660). The mechanisms that allow for efficient polarization transfer (i.e., the "solid effect" and "cross effect") may not be applicable to the liquid state. In the exemplary embodiment, the application of DNP to sensitivity enhancement in solution NMR may rely on the transfer of magnetization via a dipole-dipole Overhauser effect (OE) interaction.

Water usually absorbs strongly in the microwave region where, depending on the field employed for polarization, irradiation of the electronic transition will take place. Accordingly, this may result in significant and possibly catastrophic heating of the sample. The exemplary embodiments described in this disclosure may overcome this barrier. For example, encapsulating proteins within a protective aqueous core of a reverse micelle in order to dissolve particles in ultralow viscosity fluids may enhance NMR performance. The entire reverse micelle particle may tumble faster in the low viscosity solvent than the protein would in the relatively more viscous water/aqueous solution. The low viscosity fluids may also have the characteristic of low absorption of microwave frequencies. Thus, dielectric loss (heating) arising from saturation of the electronic transition of the radical using GHz frequencies may be avoided and/or mitigated. Reverse micelle samples may have minimal overall dielectric loss in the microwave region. Additionally, the slowed water motion relative to bulk solution may overcome very short residence time(s) of water on the surface of protein molecules, which may result in inefficient dipolar contact and poor polarization transfer to the protein. In contrast to bulk solution, the residence time of water on the surface of an encapsulated protein may be significantly longer and result in polarization transfer. The herein described reverse micelle system may also offer flexibility in how the spin radical is introduced and potentially permit the tuning of water dynamics to optimize the DNP effect.

Experiments involve polarizing a radical with microwave radiation may incorporate solvents having appropriate viscosity, solubility, and dielectric constant. In an example embodiment, the dielectric constant of the solvent may be sufficiently low to avoid heating of the sample. Solvents with low dielectric loss spectra above 1 GHz may be suitable. However, the use of DNP to enhance the NMR signal of biomaterial may be encumbered because solvents such as hydrocarbons (i.e., ethane, propane, butane, or the like) may denature the biomolecular material which results in loss of structure. Example biomolecular material may include a protein, polysaccharide, polypeptide, polynucleotide or any appropriate combination thereof. Biomolecular material may be dissolved in buffered aqueous solutions to avoid denaturing. These solvents may have high dielectric constants (for example, the dielectric constant, e, for water is approximately 80). Thus, solvents used to make solutions of biomolecular material may absorb the microwave radiation which may result in heating and damage to the biomolecule. Appropriate solvents having desired properties may depend on the solubility of the reverse micelle. Solvents may have various effective freezing points and/or boiling points.

In an example embodiment, biomolecular material may be dissolved in solvents with sufficiently low dielectric constants, such as, for example, liquid propane, pentane, hexane, ethane, or the like. This may be accomplished by encapsulating a biomolecule within the water cavity of a reverse micelle, thus allowing DNP NMR experimentation on structurally intact biomolecular material.

Figure 3:
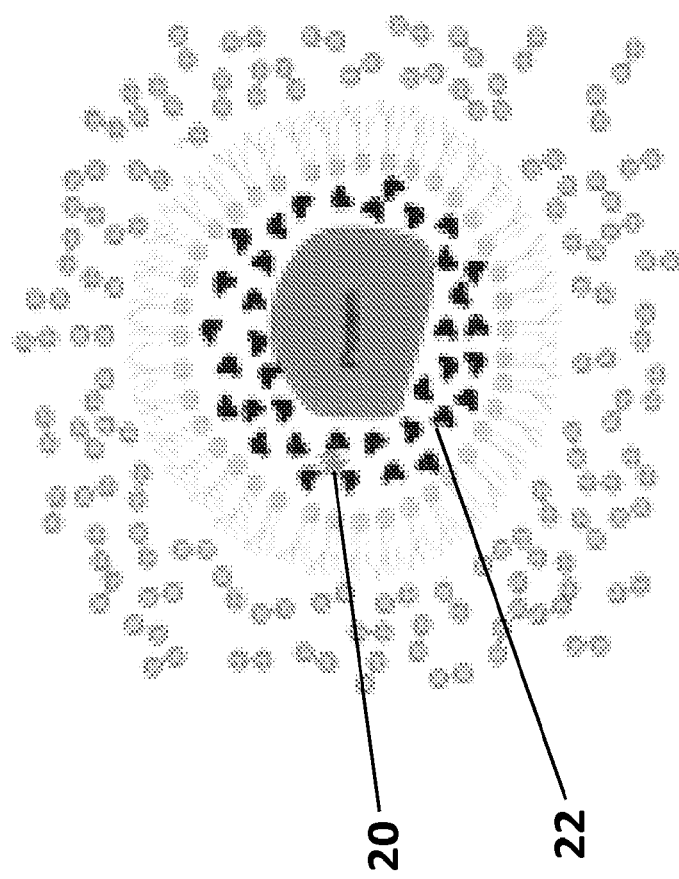
FIG. 3 illustrates encapsulating solution NMRs wherein a radical is free in a water core.
Figure 4:
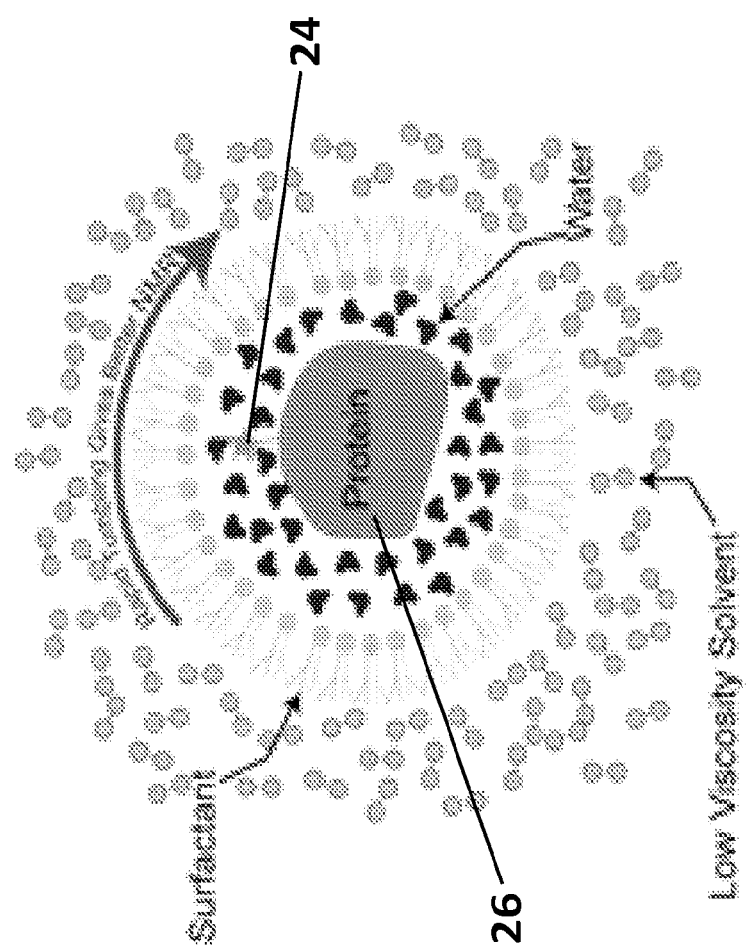
FIG. 4 illustrates encapsulating solution NMRs wherein a radical is attached to a macromolecule.
Figure 5:
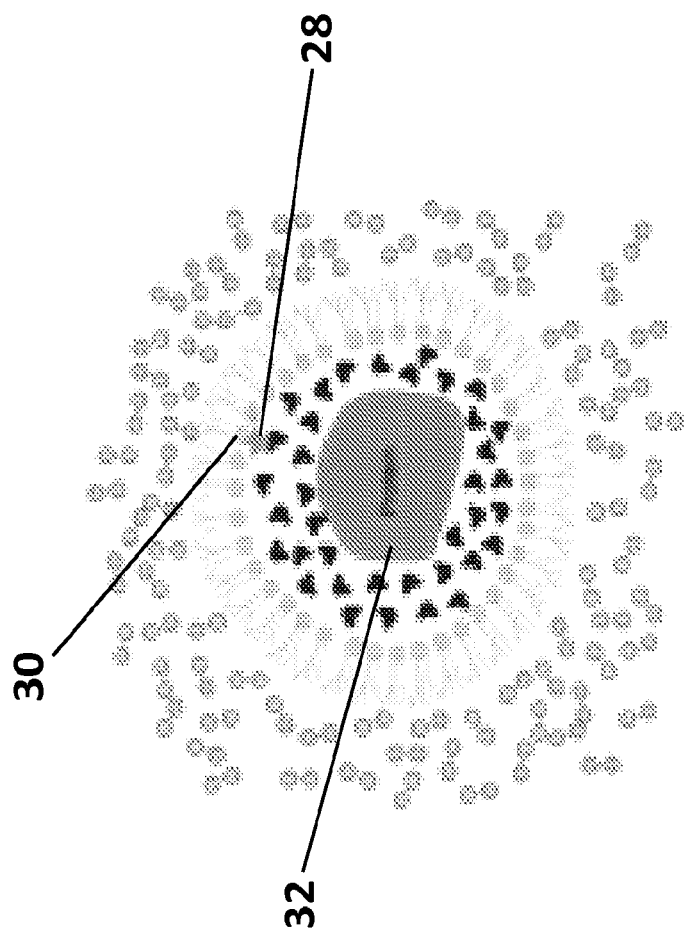
FIG. 5 illustrates encapsulating solution NMRs wherein a radical is attached to the surfactant shell of the reverse micelle.

The biomolecular material may be encapsulated within the reverse micelle and dissolved in the appropriate solvent. The reverse micelle may contain both a water core or any appropriate aqueous solution and a spin radical. Suitable spin radicals may include nitroxide radicals such as TEMPOL and TEMPONE, their various derivatives, or any appropriate combination thereof. As described above, radicals (e.g., spin radicals) may be introduced into the reverse micelle system by attaching the radical to the protein, embedding the radical in the reverse micelle shell, introducing radicals free in the aqueous core, or any appropriate combination thereof. FIG. 3 illustrates encapsulating solution NMRs wherein a radical 20 is free in a water core 22. FIG. 4 illustrates encapsulating solution NMRs wherein a radical 24 is attached (e.g., bonded) to a macromolecule 26. FIG. 5 illustrates encapsulating solution NMRs wherein a radical 28 is attached (e.g., bonded) to a surfactant shell 30, wherein the radical 28 is oriented inwards toward the biomolecule 32.

Once a sample is prepared, the reverse micelle solution may be subjected to a magnetic field to be polarized. The reverse micelle may be subjected to a magnetic field having an appropriately high magnetic field strength and the appropriate electromagnetic radiation may be applied. The electromagnetic radiation used to saturate the electronic transitions of the spin radical in the magnetic field may be above 1 GHz. The saturation of the spin radical may lead to the polarization of nuclear spins of the hydrogen atoms in the water core. This in turn may lead to polarization of the nuclear spins of the biomolecule. Normally, the transfer of polarization from the polarized water to the biomolecule is very inefficient in a biomolecule solution in bulk water. In a reverse micelle, transfer of polarization from the polarized water to the biomolecule may occur more quickly than a transfer of polarization from polarized water to a biomolecule in bulk water. The water in the core of the micelle may be slowed by approximately two orders of magnitude. Slower transfer may result in more efficient transfer of polarization from water to the biomolecule.

Figure 6:
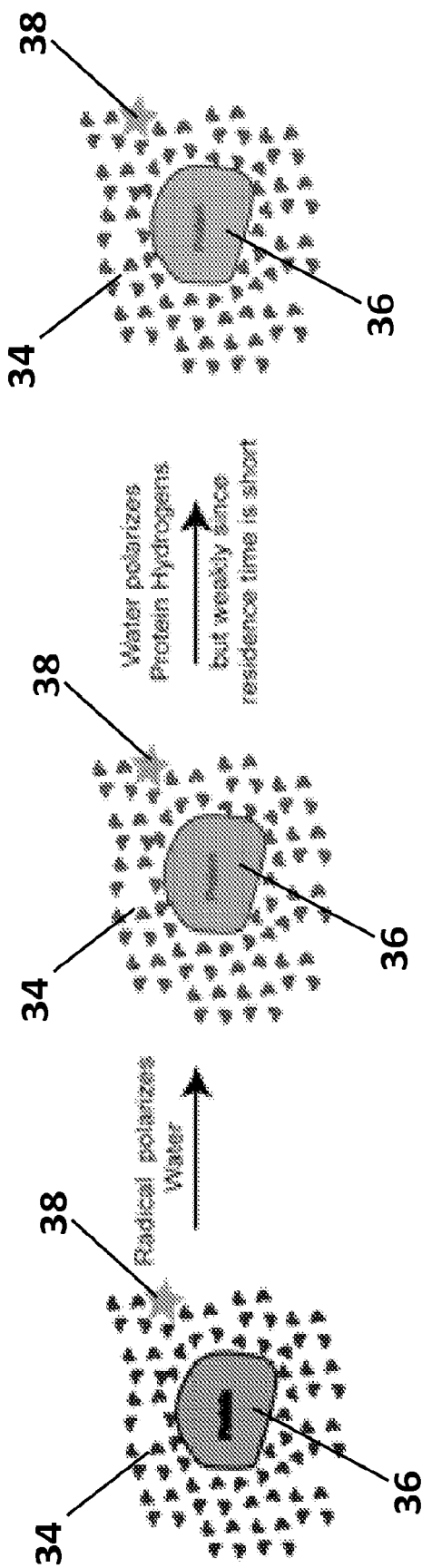
FIG. 6 illustrates transfer of polarization from water to a protein in a free water solution.

FIG. 6 illustrates the transfer of polarization from water 34 to a protein 36 in a free water solution. As depicted in FIG. 6, a radical (e.g., spin radical) 38 polarizes water 34 (e.g., polarizes the hydrogen molecules of the water 34). And the polarized water 34 polarizes the protein 36 (e.g., polarized the hydrogen nuclei of the protein 36). The polarization of the protein 36 is weak however, because the residence time is short. In a free water solution, there is poor transfer between the surrounding water 34 molecules and the biomolecule 36 because the water 34 molecules do not reside on the surface of the protein 36 for a sufficient enough time to effectuate strong polarization transfer.

Figure 7:
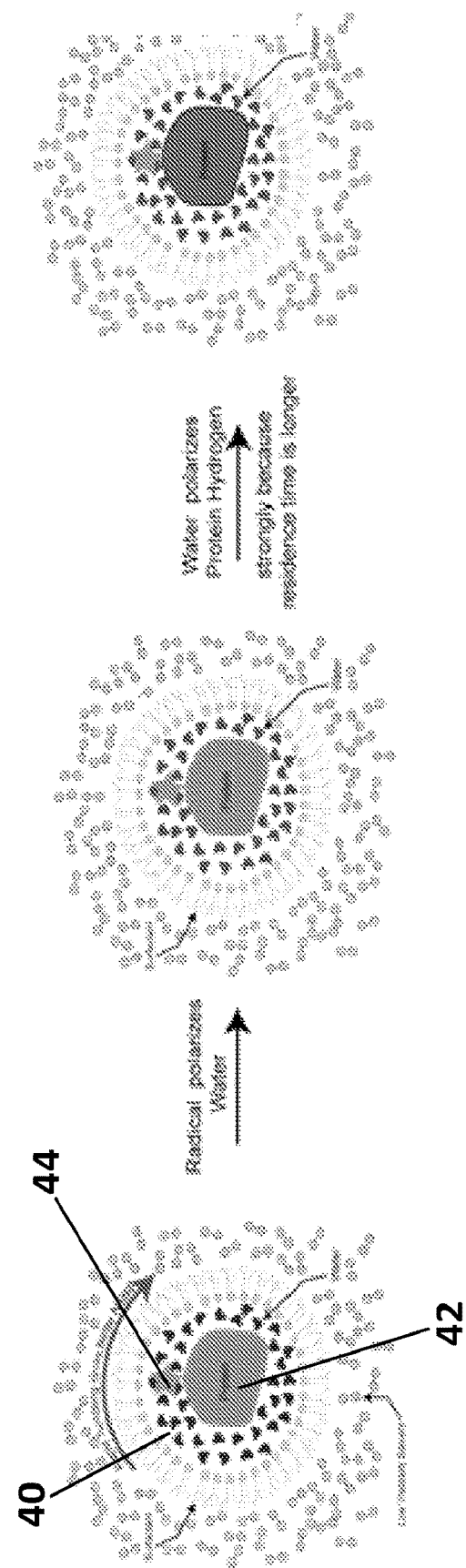
FIG. 7 illustrates the transfer of polarization from water or any appropriate aqueous solution to a protein encapsulated in a reverse micelle.

FIG. 7 illustrates the transfer of polarization from water 40 to a protein 42 encapsulated in a reverse micelle. As depicted in FIG. 7, a radical (e.g., spin radical) 44 polarizes water 40 (e.g., polarizes the hydrogen molecules of the water 40). And the polarized water 40 polarizes the protein 42 (e.g., polarized the hydrogen molecules of the protein 42). The polarization of the protein 42 is stronger (as compared to the situation depicted in FIG. 6) however, because the residence time is longer (as compared to the situation depicted in FIG. 6). Water 40 within the encapsulated micelle resides on the surface of the biomolecule 42 for longer periods of time and polarization can be more efficiently transferred to the biomolecule 42.

In an example embodiment, electromagnetic radiation may be applied to the spin radical until there is significant saturation. Significant saturation of the spin radical may occur when the polarization of the spin radical can be transferred to the surrounding water molecules. Greater saturation of the spin radical may lead to greater transfer of polarization from the radical to the water and subsequently to the encapsulated molecule of interest leading to improved sensitivity. The nuclear spin transitions of the polarized biomolecule may then be detected.

In example embodiments, radicals (e.g., spin radicals) may be polarized in a first magnetic field strength and nuclear spin transitions of polarized biomolecules be detected at a higher magnetic field strength. The first magnetic field strength may allow for the use of electromagnetic radiation at a lower frequency than that required if saturation of the electronic transition were carried out at a higher magnetic field. This way, heating of the sample may be avoided or reduced. Once the spin radical is polarized at the lower magnetic field, the encapsulated biomolecule may be subsequently subjected to the higher magnetic field to detect the nuclear spin transitions. In an example embodiment, the encapsulated biomolecule is shuttled (e.g., spatially moved) from the first magnetic field to the second magnetic field. The time difference between completion of application of the electromagnetic radiation and subjecting the reverse micelle solution to a second magnetic field strength may be short enough to preserve the excess polarization.

Figure 8:
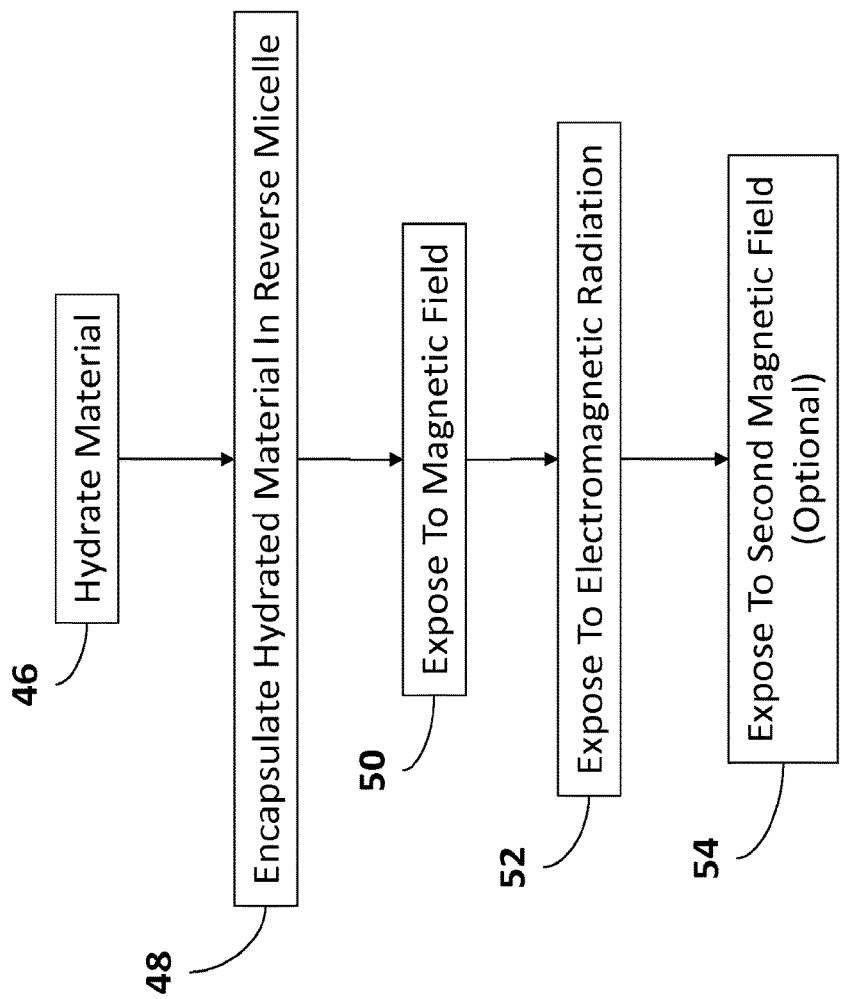
FIG. 8 is a flow diagram of an example process for implementing enhanced nuclear spin polarization.

FIG. 8 is a flow diagram of an example process for implementing enhanced nuclear spin polarization. A material may be hydrated at step 46. As described herein, the material may comprise any appropriate material, such as, for example, a water soluble material. Example materials may comprise, for example, a biomaterial, a protein, a polysaccharide, a polypeptide, a polynucleotide, or the like, or any appropriate combination thereof.

At step 48, the hydrated material may be encapsulated in a reverse micelle as described herein. Hydrating the material may comprise hydrating the material in water or hydrating the material in any appropriate aqueous solution. Also as described herein, the reverse micelle may comprise a radical(s). The reverse micelle may comprise any appropriate radical(s). An example radical may comprise, for example, any appropriate spin radical, any appropriate nitroxide radical, TEMPOL, any appropriate derivate of TEMPOL, TEMPONE, any appropriate derivate of TEMPONE, or the like, or any appropriate combination thereof. In an example embodiment, a solution of reverse micelles having respective encapsulated hydrated material may be generated. The radical(s) may be incorporated in the reverse micelle in any appropriate manner. For example, as described herein, the radical(s) may be free in a water core of the reverse micelle, the radical(s) may be attached (e.g., bonded) to a macromolecule of the reverse micelle, the radical(s) may be attached (e.g., bonded) to a surfactant shell of the reversed micelle wherein the radical is oriented inwards toward the material encapsulated in the reverse micelle, or the like, or any appropriate combination thereof. In an example embodiment, the reverse micelle may be dissolved in a low dielectric loss solvent (e.g., ethane, propane, butane, etc.) as described herein. At step 50, as described herein, the reverse micelle and solvent solution may be exposed to a magnetic field. At step 52, as described herein, the reverse micelle and solvent solution may be exposed to electromagnetic radiation. In an example embodiment as described herein, the reverse micelle and solvent solution concurrently may be exposed to the magnetic field and the electromagnetic energy. In an example embodiment, optionally, as described herein, the reverse micelle and solvent solution may be exposed to a second magnetic field at step 54. The reverse micelle and solvent solution may be exposed to the second magnetic field in any appropriate manner. For example, the second magnetic field may be applied in place, the reverse micelle and solvent solution may be shuttled (e.g., spatially moved) from the magnetic field (step 50) to the second magnetic field (step 54), or any appropriate combination thereof.

EXPERIMENTS

Experiments were conducted utilizing enhanced nuclear spin polarization as described herein. This experiment example refers to an exemplary protein expression and spin labeling. The C55A mutant of flavodoxin from C. anabaena PCC7119 was expressed during growth on minimal media containing $NH_4Cl$. This protein was used for studies where the nitroxide spin label was either free in the aqueous core of the reverse micelle or attached to a lipid embedded in the reverse micelle surfactant shell. In this example, the $^{15}N$ flavodoxin (C55A) with the flavin mononucleotide bound was concentrated to 6.5 mM in 10 mM Tris buffer and 100 mM NaCl at pH 8.0 for reverse micelle sample injection. To covalently attach a nitroxide spin label to the protein, a surface accessible cysteine mutant of flavodoxin (C55A, S72C) was generated by site directed mutagenesis and confirmed by DNA sequencing. Uniformly $^{15}N$-labeled flavodoxin (C55A, S72C) was expressed and purified, wherein 1 mM dithiothreitol (DTT) was present throughout the purification to prevent dimerization. In this example, Flavodoxin (C55A, S72C) was covalently labeled with $^{15}N$-(1-oxyl-2,2,5,5-tetramethyl-D3-pyrroline-3-methyl)-methanethiosulfonate (MTSL) (Toronto Research Chemicals) using published protocols. [13], [14] A 10 fold excess of MTSL in acetonitrile was added to a 1 mM solution of $^{15}N$ flavodoxin (C55A, S72C) in 10 mM Tris buffer and 100 mM NaCl at pH 8.0. No DTT was used at this point. In this example, the reaction was allowed to proceed for 16 hours at room temperature under argon. The excess reagent was removed by repetitive ultrafiltration.

Solutions of reverse micelles were made with a surfactant mixture containing a 65:35 molar ratio of 1-decanoyl-rac-glycerol (10MAG) (Sigma-Aldrich, Co., LLC) and lauryldimethylamine-N-oxide (LDAO) (Affymetrix, Inc.), at 100 mM concentration, 5 mM d-11-hexanol dissolved in d-14 hexane with a molar ratio of water to total surfactant molecules ($W_o$ or water loading) of 20. LDAO and 10MAG combined in the prescribed ratio as dry powders, dissolved in hexane, bath sonicated to promote dissolution and lyophilized in glass vials. The lyophilized dry mixture was dissolved in 0.5 mL deuterated hexane and made 5 mM in deuterated hexanol (0.3 μL). An aqueous aliquot equivalent to a water loading of 20 (18.2 μL) was injected and then vortexed, resulting in a clear solution. This procedure was followed to prepare reverse micelles containing flavodoxin-MTSL adducts or flavodoxin with TEMPOL dissolved in the aqueous core. In the latter case the protein and TEMPOL were prepared in a molar ratio of 0.85:1.0. In this example, reverse micelles containing the surfactant nitroxide spin label TEMPO-PC (1,2-dipalmitoyl-snglycero-3-phosphocholine (Avanti Polar Lipids, Inc.) was prepared as elsewhere in this disclosure with the additional step of cosolubilizing the TEMPO-PC with the 10MAG and LDAO surfactant mixture in final concentrations of 0.6 mM, 65 mM and 35 mM, respectively. The TEMPO-PC was purchased as 1 mg/ml in $CHCl_3$. An appropriate aliquot was lyophilized in a glass vial and combined with the 10MAG and LDAO aliquot dissolved in hexane. The resulting solution was vortexed and lyophilized again. The dry surfactant mixture was dissolved in 500 μL of deuterated hexane and 0.3 μL of deuterated hexanol. This solution was injected with 18.2 μL of buffer or 6.8 mM $^{15}N$ flavodoxin C55A, as required, and vortexed until a clear solution formed.

$^{15}N$ HSQC spectra were collected on an AVANCE III 600 MHz Bruker spectrometer equipped with a TCI cryoprobe. In this example, two-dimensional spectral acquisitions included 1024 complex points in the $^1H$ direct dimension and 200 complex points in the $^{15}N$ indirect dimension. All spectra were obtained at 25° C. Data were processed using the AL NMR processing package. The SPARKY graphical analysis software was used to tabulate resonance assignments and associated intensities.

Paramagnetic relaxation enhancement (PRE) values were determined from the ratio of HSQC intensities of amide $^{15}N$-$^1H$ correlations in the reverse micelle samples with oxidized (paramagnetic) and reduced (diamagnetic) nitroxide spin label. In this example, PRE ratios were normalized to 1.0 using an average scaling factor from the cross peak intensities of the resonances unaffected by the presence of the spin label. Samples were reduced with ascorbate. The $^{15}N$ and $^1H$ chemical shift assignments for $^{15}N$ labeled flavodoxin (C55A, S72C) were mapped from the aqueous flavodoxin assignments. Mapped assignments were confirmed by tracing the through space connectivities in a 3D NOESY HSQC spectrum collected with a 125 ms (millisecond) mixing time. Samples employing TEMPOL in the water core or TEMPO-PC in the surfactant shell of the reverse micelle were made with $^{15}N$-flavodoxin (C55A). The reverse micelle samples with the spin label covalently attached to the protein were prepared with $^{15}N$-MTSL-$^{15}N$flavodoxin (C55A, S72C).

Water saturation experiments were implemented with a selective irradiation pulse preceding the first $^1H$ RF preparation pulse of the INEPT transfer in the HSQC experiment. In this example, the saturation pulse was applied at the water resonance frequency for the duration of the recycle delay, 1 second, at a series of field strengths ranging from 50 Hz (0.008 mW at 600 MHz) through 250 Hz (0.190 mW at 600 MHz).

Estimates of the effective macromolecular tumbling time of the encapsulated protein were obtained from the $^{15}$N-TRACT measurements using 40 gradient time increments to describe the decay of the relevant $\alpha$ and $\beta$ $^{15}$N transitions. Exponential decay rates of selected regions of the integrated amide frequencies were fitted using in-house python scripts with Al NMR processing.

CW EPR spectra were acquired on a Bruker EMX spectrometer operating at 9.4 GHz. In this example, spectra were collected with a 100 G sweep width and a 100 kHz modulation frequency using 1 mW of power. Power saturation EPR curves were collected to the maximum available power (300 mW). All reverse micelle solutions tolerated this power. Aqueous solutions were susceptible to boiling at power levels elsewhere in this disclosure 100 mW. Large diameter (4 mm) EPR tubes were used for data collection of reverse micelle solutions at room temperature. The EPR spectra of aqueous solutions were collected in Wiretrol 50 μL capillary tubes (Drummond Scientific Co.).

DNP enhancements of the water resonance were recorded using a Bruker 9.4 GHz X-band ENDOR spectrometer modified with a Spincore NMR console operating at 14.7 MHz for $^1$H NMR acquisition with an ENI LPI10 amplifier for the $^1$H RF pulses. In this example, the probe was an MD4-W1 ENDOR cavity with an $^{15}$N and $^1$H double tuned NMR coil. The microwave saturation was applied with a Bruker AMPX10 amplifier that delivers 10 Watts CW at 9.4 GHz. The DNP enhancement was recorded with the microwave applied continuously at 10 Watts during the $^1$H RF pulse, FID acquisition and recycle delay. Spectral acquisitions included 128 scans with a 10 kHz sweep width and 512 complex points, with an interscan delay of 4 seconds using a cyclops quadrature phase cycle of the 90 degree RF pulse and receiver phase. The microwave CW frequency was set to the frequency of the down field component of the hyperfine multiplet from the EPR spectrum. Since the ENDOR spectrometer operates without a field frequency lock, the NMR spectrum was centered at the calculated field based on the frequency of the EPR transition and the gyromagnetic ratios of the electron and proton spins. The spectra were recorded with and without the application of the microwave power. The signal phase was negative for the spectra with the "microwave on" compared to the "microwave off" spectra, confirming the Overhauser enhancement mechanism for the DNP effect. The DNP spectra were processed with an exponential multiplication of 10 Hz, zero filled once and Fourier transformed.

Figure 9:
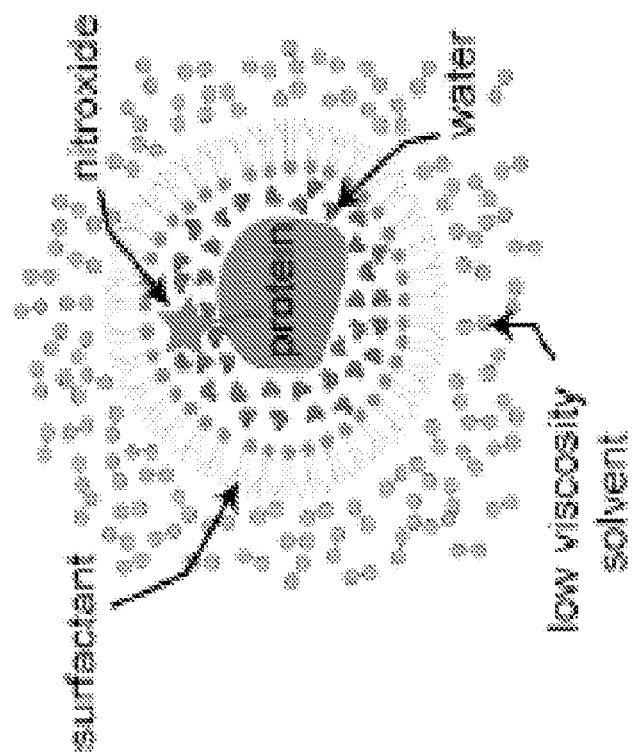
FIG. 9 depicts a nitroxide radical covalently attached to a protein.
Figure 10:
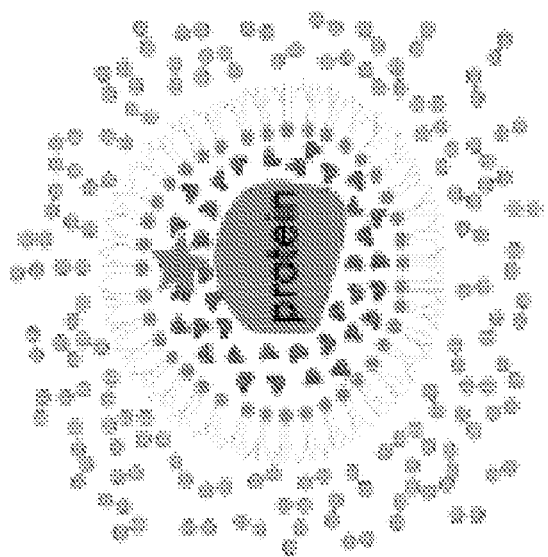
FIG. 10 depicts a nitroxide radical dissolved in an aqueous core.
Figure 11:
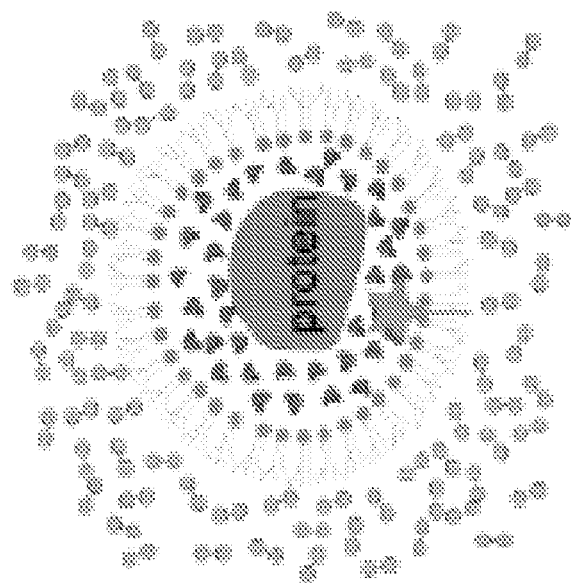
FIG. 11 depicts a nitroxide radical covalently attached to a carrier embedded in the surfactant shell of the reverse micelle.

FIG. 9, FIG. 10, and FIG. 11 depict schematic illustrations of the strategies for introduction of nitroxide spin radicals to reverse micelles. FIG. 9 depicts Nitroxide covalently attached to the protein (MTSL). FIG. 10 depicts Nitroxide dissolved in the aqueous core (TEMPOL). FIG. 11 depicts Nitroxide covalently attached to a carrier embedded in the surfactant shell (TEMPO-PC).

To examine the potential for reverse micelle samples to provide a path to signal enhancement, as depicted in FIG. 9, FIG. 10, and FIG. 11, three types of placement of nitroxide spin radical in the reverse micelle macromolecular assembly may be used: attachment to the protein via a cysteine bridge (MTSL); embedded in the reverse micelle shell using a carrier lipid (TEMPO-PC); and (3) free in the aqueous core in soluble form (TEMPOL).

Mutants of flavodoxin from C. anabaena PCC7119 as a test protein were used. Flavodoxins function as soluble electron carriers between redox proteins and contain a noncovalently bound flavin mononucleotide cofactor (FMN) that serves as a redox center and are characterized by an $\alpha/\beta$ doubly wound topology, which consists of a five-stranded parallel beta-sheet surrounded by $\alpha$-helices on both sides. In this example, the C55A mutant from C. anabaena PCC7119 was used as a parent molecule in order to avoid slow dimerization through an intermolecular disulfide. For direct ligation of the nitroxide radical to the protein, flavodoxin (C55A, S72C) was created to provide a readily accessible surface cysteine through which a nitroxide spin radical (MTSL) could be attached using standard chemistry. The protein comprises 179 amino acid residues and has a non-covalently but tightly bound flavin mononucleotide (FMN) cofactor. In this example, a surfactant system based on the on the zwitterionic surfactant lauryldimethylamine-N-oxide (LDAO) and the nonionic surfactant 1-decanoyl-rac-glycerol (10MAG) was employed. Conditions were chosen to have roughly one nitroxide radical per protein-containing reverse micelle to avoid Heisenberg exchange interactions between nitroxide spin radicals.

Figure 12:
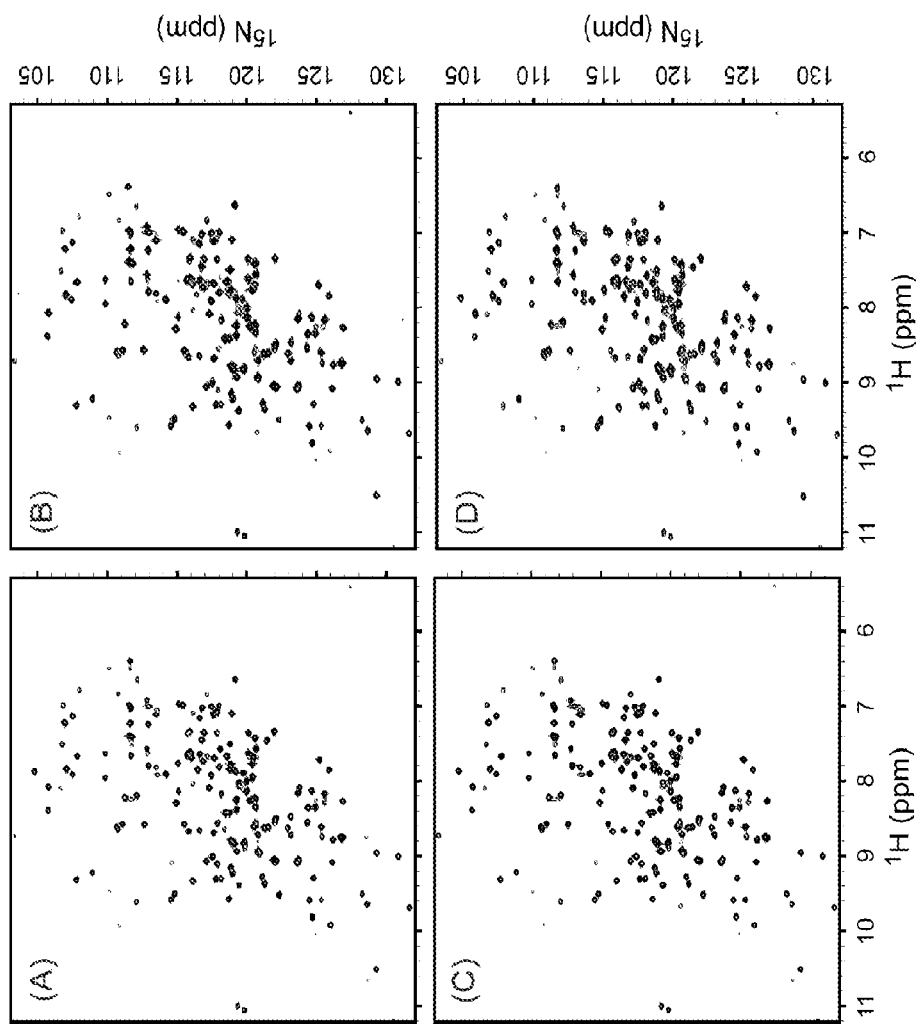
FIG. 12, which include Graph (A), Graph (B), Graph (C), and Graph (D), illustrates the structural integrity of encapsulated spin labeled flavodoxin.

FIG. 12, which include graphs (A), (B), (C), and (D), illustrates the structural integrity of encapsulated spin labeled flavodoxin. FIG. 12, graph (A) illustrates an exemplary $^{15}$N HSQC spectra of $^{15}$N flavodoxin (C55A) where structural integrity of encapsulated spin labeled flavodoxin is maintained. FIG. 12, graph (B) illustrates an exemplary $^{15}$N HSQC spectra of $^{15}$N flavodoxin (C55A, S72C) with oxidized $^{15}$N MTSL covalently attached where structural integrity of encapsulated spin labeled flavodoxin is maintained. FIG. 12, graph (C) illustrates an exemplary $^{15}$N HSQC spectra of $^{15}$N flavodoxin C55A with oxidized TEMPOL spin label where structural integrity of encapsulated spin labeled flavodoxin is maintained. FIG. 12, graph (D) illustrates an exemplary $^{15}$N HSQC spectra pf $^{15}$N flavodoxin (C55A) with oxidized TEMPOPC where structural integrity of encapsulated spin labeled flavodoxin is maintained.

Figure 13:
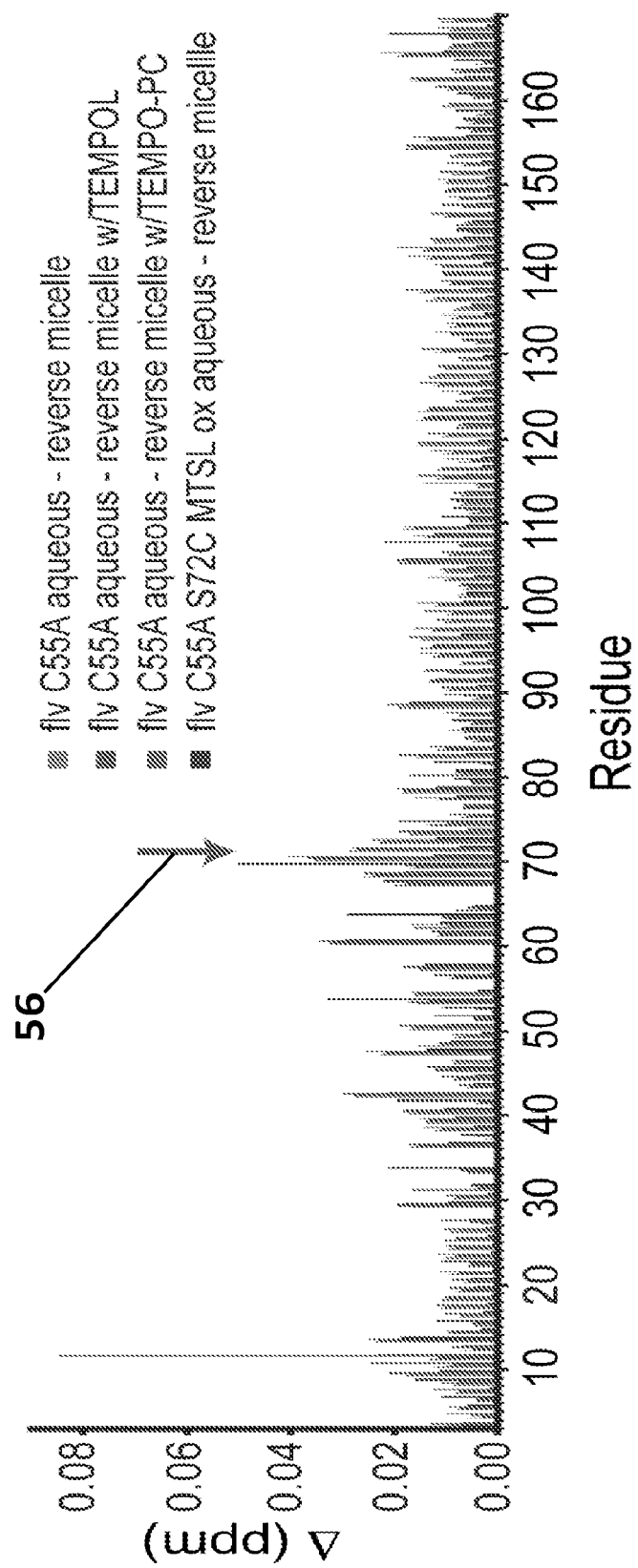
FIG. 13 illustrates an exemplary correlation plot of chemical shift differences further illustrating the structural integrity of encapsulated spin labeled flavodoxin.

FIG. 13 illustrates an exemplary correlation plot of the chemical shift differences, such as calculated by:

$$\Delta = \sqrt{\left(\frac{\Delta\delta_N \gamma_H}{\gamma_H}\right)^2 + (\Delta\delta)^2}$$

between the flavodoxin in free aqueous solution and the corresponding flavodoxin in LDAO/10MAG reverse micelles. All residues that could be measured are shown including the site of mutation and ligand attachment (as indicated by arrow 56 in FIG. 13). In this exemplary embodiment, very minor chemical shift perturbations were found ($R^2=0.999$ and $<r.m.s.d.>=0.010$) indicating that high structural fidelity is maintained upon encapsulation of the protein with spin label in the three labeling scenarios examined.

As illustrated in FIG. 12, graphs (A), (B), (C), (D), and FIG. 13, the protein and corresponding spin label were encapsulated within LDAO/10MAG reverse micelles in pentane with a water loading of 20. Detailed consideration of the $^{15}$N-HSQC spectra of encapsulated flavodoxin in the three scenarios for delivery of the nitroxide radical to the reverse micelle indicates that the structural integrity of the protein is fully maintained.

Figure 14:
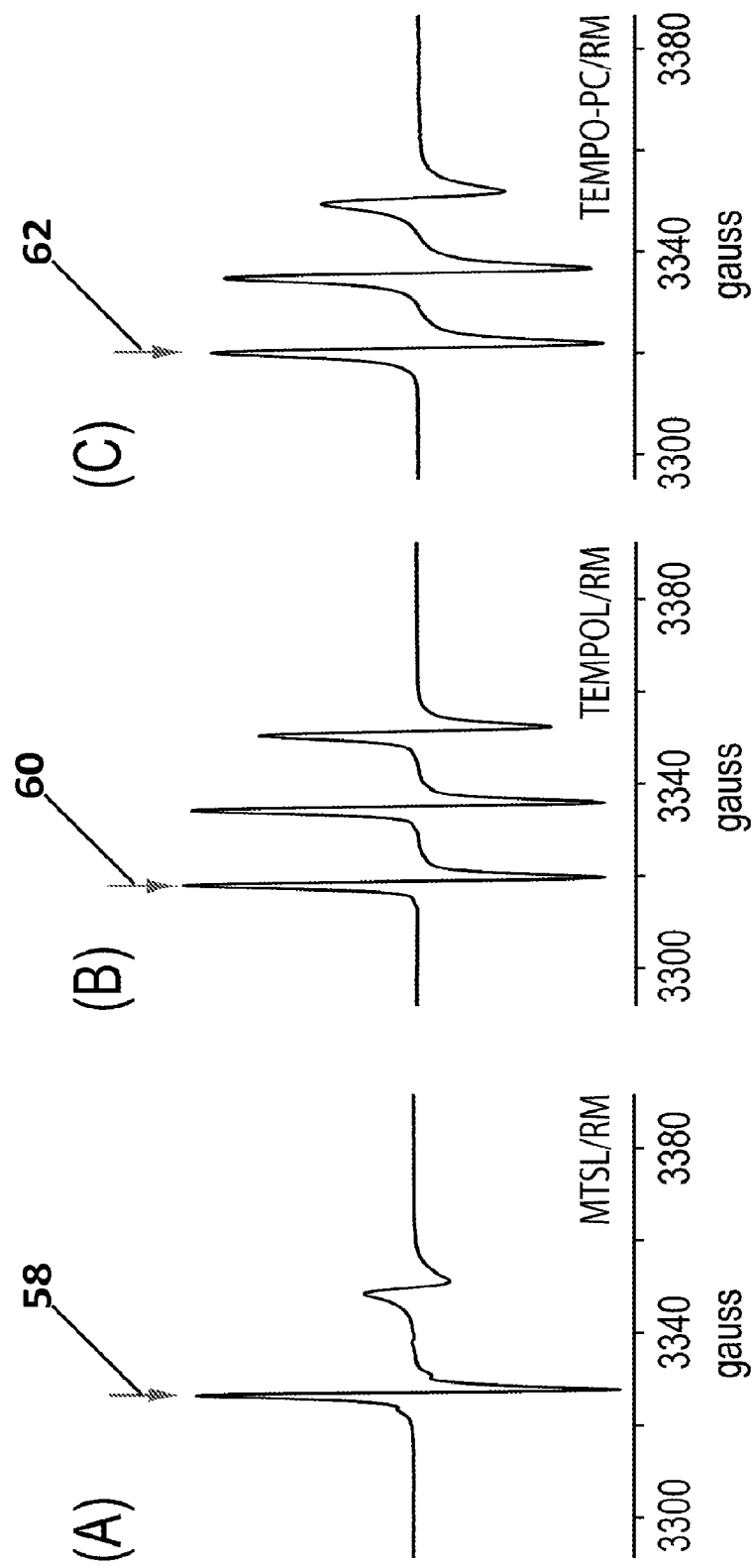
FIG. 14, which includes Graph (A), Graph (B), and Graph (C), illustrates electron paramagnetic resonance spectra of encapsulated nitroxide labeled flavodoxin illustrating that sample tube diameter or total sample volume is not limited by the production of heat.

FIG. 14, which includes graph (A), graph (B), and graph (C), illustrates an exemplary embodiment where reverse micelle solutions do not limit sample tube diameter or total sample volume. FIG. 14 further illustrate X-band EPR spectra of the three exemplary nitroxide labeling scenarios. The general strategy that has been followed for the implementation of dynamic nuclear polarization in aqueous solution is to utilize the rapidly fluctuating interaction of solvent water and spin radical to mediate polarization transfer through the OE. In addition, the second and equally important polarization transfer between water and the macromolecule of interest will also proceed via a dipole-dipole interaction albeit with somewhat different physical parameters. To achieve sensitivity enhancement, it may be important that sample size not be overly compromised. Unfortunately, the high dielectric loss of standard aqueous samples requires significant reduction in both sample volume and depth. In contrast, solutions of reverse micelles in liquid alkane solvents are relatively transparent to GHz frequencies. Though the water core of reverse micelles can have significant dielectric absorption in this frequency region, the overall bulk macroscopic property of microwave receptivity of reverse micelle solutions are much more favorable than aqueous solutions.

In contrast, aqueous sample volumes and tube diameters are kept an order of magnitude smaller for even simple EPR spectra to be obtained. In the context of DNP, optimized coil designs with very small sample sizes on the order of μL to nL is employed. In this exemplary embodiment, this creates at the outset a deficit in signal-to-noise that must be overcome in order for DNP to ultimately prove worthwhile.

FIG. 14 graph (A), graph (B), and graph (C) further illustrates X-band (9.4 GHz) EPR spectra of the nitroxide spin radical in the three labeling scenarios in LDAO/10MAG reverse micelles. FIG. 14 graph (A) illustrates X-band (9.4 GHz) EPR spectra of the nitroxide spin radical in labeling $^{15}$N-flavodoxin in the aqueous core and covalently attached to $^{15}$N-MTSL. FIG. 14 graph (B) illustrates X-band (9.4 GHz) EPR spectra of the nitroxide spin radical in labeling $^{14}$N-TEMPOL solubilized in the aqueous core with $^{15}$N-flavodoxin. FIG. 14 graph (C) illustrates X-band (9.4 GHz) EPR spectra of the nitroxide spin radical in labeling $^{15}$N-flavodoxin and $^{14}$N-TEMPO-PC solubilized in the reverse micelle surfactant shell. The triplet splitting is a result of the spin 1 $^{14}$N-electron hyperfine coupling for $^{14}$NTEMPO-PC and $^{14}$N-TEMPOL while the doublet splitting arises from the spin ½ $^{15}$N-electron hyperfine coupling of the $^{15}$N-MTSL. These spectra were obtained at 25° C. with 4 mm sample tubes. Arrows 58, 60, and 62, indicate respective frequencies for the application of the microwave power for the DNP experiments.

As illustrated in FIG. 14 graph (A), graph (B), and graph (C), the EPR spectra indicate that the nitroxide moiety experiences variable dynamics depending on context. For example, the broadening evident in the spectra of MTSL and TEMPO-PC indicate relatively restricted motion compared to TEMPOL free in the aqueous core of the reverse micelle. This may have important implications for subsequent optimization of the primary DNP to the water core.

Figure 15:
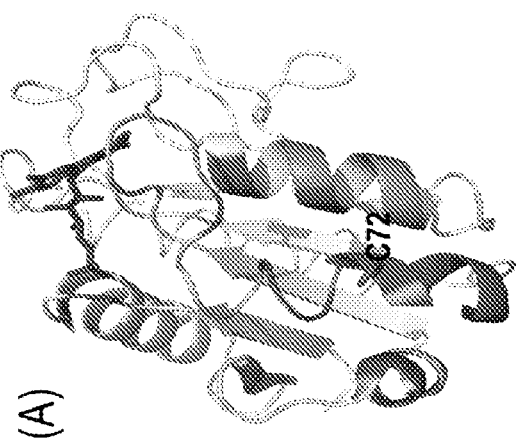
FIG. 15, which includes
Figure 15:
Figure 15:
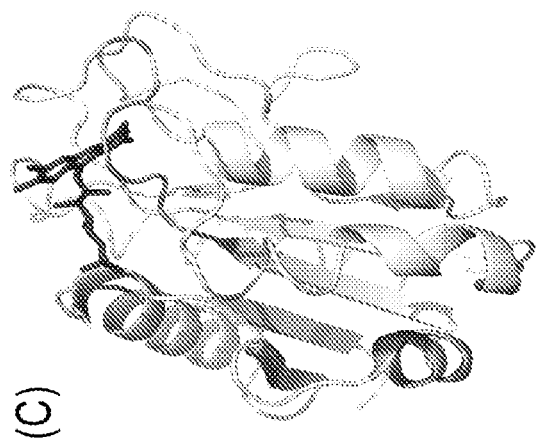

FIG. 15, which includes FIG. 15A, FIG. 15B, and FIG. 15C, illustrates paramagnetic relaxation effects. Further analysis also showed the expected presence of paramagnetic relaxation enhancement (PRE) effects. PREs can potentially counter the desired DNP signal enhancement through introduction of line broadening and other relaxation effects. The deleterious effects of the PRE here arise primarily from long range coupling of the electron spin with $^1$H spins. Accordingly, attention is paid to the placement of the nitroxide spin radical. FIG. 15A illustrates an exemplary embodiment where Paramagnetic relaxation effects where MTSL spin label covalently attached to C72 of flavodoxin (C55A, S72C) gave significant PREs in accordance with expected distant dependence in the region encompassing ~15 Å distances to the spin label. A number of amide $^{15}$N-$^1$H correlations have greatly diminished intensity. This initial result recommends against employing a covalently attached spin radical in the context of DNP utilizing reverse micelle encapsulation. In contrast, FIG. 15B and FIG. 15C, where nitroxide radical is solubilized within the aqueous core or restricted to the surfactant shell, show minimal PRE effects.

Figure 16:
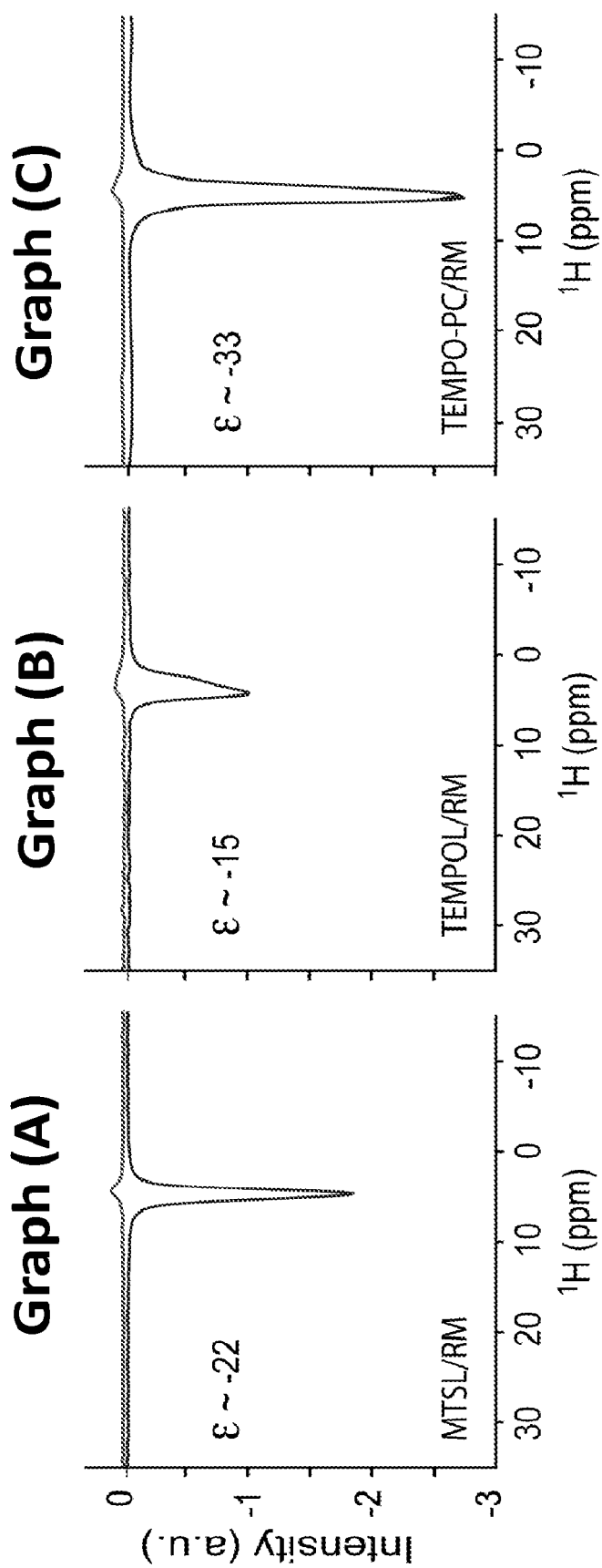
FIG. 16, which includes Graph (A), Graph (B), and Graph (C), illustrates dynamic nuclear polarization of the water core in reverse micelles.

FIG. 16, which includes Graph (A), Graph (B), and Graph (C), illustrates dynamic nuclear polarization in reverse micelles. FIG. 16 Graph (A) illustrates an exemplary Dynamic nuclear polarization in reverse micelles specifically $^1$H NMR spectra (14.7 MHz) of the water core of LDAO/10MAG reverse micelles with (blue) and without (red) saturation of the 9.4 GHz EPR transition illustrated in FIG. 14 for $^{15}$N-flavodoxin covalently attached to $^{15}$N-MTSL and dissolved in the aqueous core. FIG. 16 Graph (B) illustrates an exemplary dynamic nuclear polarization in reverse micelles specifically $^1$H NMR spectra (14.7 MHz) of the water core of LDAO/10MAG reverse micelles with (blue) and without (red) saturation of the 9.4 GHz EPR transition illustrated in FIG. 14 for $^{14}$N-TEMPOL solubilized in the aqueous core with $^{15}$Nflavodoxin. FIG. 16 Graph (C) illustrates an exemplary Dynamic nuclear polarization in reverse micelles specifically $^1$H NMR spectra (14.7 MHz) of the water core of LDAO/10MAG reverse micelles with (blue) and without (red) saturation of the 9.4 GHz EPR transition illustrated in FIG. 14 for $^{15}$N-flavodoxin in the aqueous core and $^{14}$NTEMPO-PC solubilized in the reverse micelle (RM) surfactant shell.

DNP enhancement factors ($\in$) were determined from the ratio of the measured intensities of the water resonance in the $^1$H NMR spectra recorded at 14.7 MHz with and without irradiation of the downfield hyperfine transition. In the example embodiment, microwave power at 9.4 GHz was applied continuously at 10 W for 4 seconds. The resulting $^1$H spectra and enhancements are illustrated in FIG. 16, Graph (A), Graph (B), and Graph (C). TEMPOL free in the water core of the reverse micelle gave the lowest net enhancement ($\in$=−15 without protein encapsulated and −15.2 with protein encapsulated), the MTSL attached to flavodoxin an intermediate enhancement ($\in$=−22) and the TEMPO-PC embedded in the reverse micelle surfactant shell the largest enhancement ($\in$=−35) without protein encapsulated and −33 with protein encapsulated). For comparison, under the same experimental conditions (except for a smaller sample size), TEMPOL in bulk aqueous solution gave an enhancement of −19. The enhancement factors are insensitive to the presence or absence of encapsulated protein in the reverse micelle. In this example embodiment, these initial results suggest that productive DNP enhancements may be obtained in the reverse micelle system without compromising sample volume. They also indicate that inclusion of the nitroxide label through association with the reverse micelle surfactant shell may be useful to anchoring the spin radical to the protein or having it free in the aqueous core of the reverse micelle.

In an example embodiment, the maximum enhancements of the $^1$H resonance of the reverse micelle water core reported here are on the order of 35-fold. Free TEMPOL in aqueous solution gave a DNP enhancement of the water signal of approximately one tenth that obtained in a more optimized setup. [33] In this example embodiment, this may suggest that significantly larger enhancements are possible through further optimization of instrumentation and sample preparation.

A component effecting DNP of macromolecules, such as proteins, may be to utilize solvent water as a reservoir of excess polarization. There may be at least two potential mechanisms for transfer of non-equilibrium magnetization from water to a protein molecule: hydrogen exchange with solvent and direct dipolar contact between the spins of water and those of the protein. Hydrogen exchange may be slowed within the reverse micelle and may be rendered ineffective for this purpose. On the other hand, the motion of water within the reverse micelle also may be slowed relative to bulk aqueous solution. The residence times of hydration water in bulk solution may be generally extremely short and result in poor dipolar contact with the protein. In contrast, the slowed dynamics of water within the reverse micelle may apparently result in long residence times to allow extensive Overhauser effects between hydration water and hydrogens at the surface of the protein. This surface magnetization may then flow throughout the protein. In an example embodiment, the effectiveness of this may be important in the context of DNP where uniform transfer of polarization throughout the protein is desired.

Figure 17:
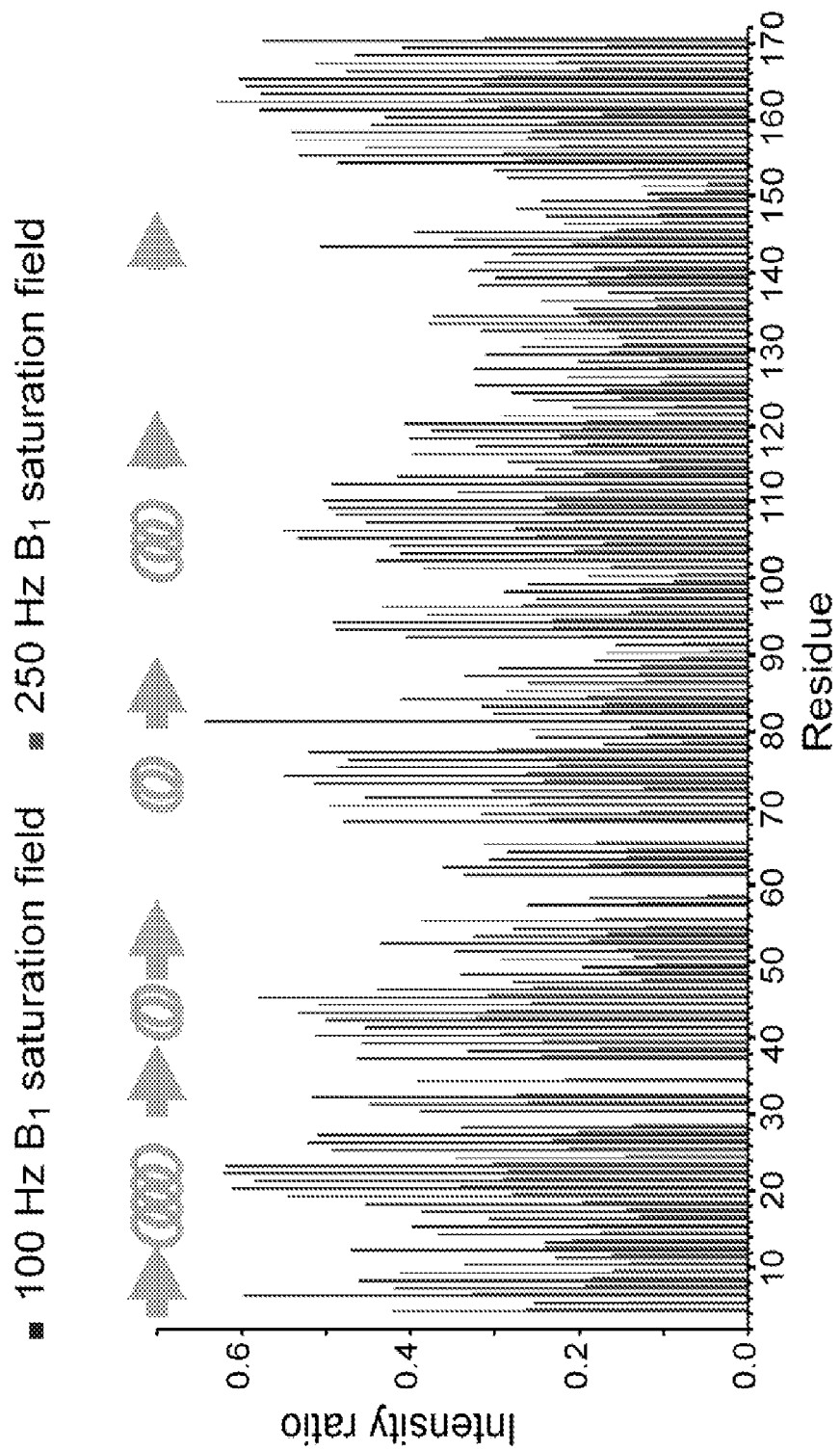
FIG. 17 illustrates efficiency of transfer of magnetization between encapsulated protein and the water core in an exemplary embodiment.

FIG. 17 illustrates efficiency of transfer of magnetization between encapsulated protein and the water core in an exemplary embodiment. In this example, the degree of saturation of amide hydrogen resonances as a function of sequence position in flavodoxin obtained with a B1 field strength of 100 Hz (0.09 mW at 600 MHz) and a B1 field strength of 250 Hz (0.19 mW at 600 MHz) applied for 1 s to the water resonance. The intensity ratio is relative to the HSQC spectrum collected without water irradiation. The secondary structure elements of the flavodoxin fold are indicated across the top of the FIG. 17.

Transfer of magnetization by (partial) saturation of the resonance of the water core to the amide hydrogens of encapsulated flavodoxin (C55A) was monitored by comparing cross peak intensities of $^{15}$N-HSQC spectra obtained with and without irradiation of the water resonance. A selective saturation pulse preceding the INEPT transfer was applied during the one second recycle delay of the HSQC experiment.

FIG. 17 further illustrates the flow of non-equilibrium magnetization from water to the protein, as the response of selective saturation of the water resonance is followed. Spectra acquired with and without the water-saturating RF pulse provide a simple measure of the efficiency of the dipolar spin exchange mechanism throughout the protein. It should be noted that, in the example embodiment, under the conditions used here, the encapsulated flavodoxin has an effective macromolecular reorientation time of ~12 ns.

The intensities of the amide hydrogen resonances may scale with the strength of the RF field applied to the water resonance. Relatively weak RF fields may lead to significant reduction in signal intensity and a $B_1$ field of 250 Hz may nearly obliterate the amide hydrogen region of the spectrum. As illustrated in FIG. 17, the saturation effect is roughly uniform with amide hydrogens located in rigid regular secondary structure or situated in dynamic regions being significantly affected. The transfer of nonequilibrium magnetization may not be limited to the surface residues of the protein, but rather dissipates to the inner core of the encapsulated protein. This may provide direct evidence that initial NOE contact between polarized water spins is sufficient to transmit magnetization to the encapsulated protein and that subsequent spin diffusion between hydrogens of the protein is sufficient to spread the polarization throughout the protein.

The initial results in the experiments described herein suggest that the use of reverse micelle encapsulation may be used in the implementation of DNP in liquids. Solutions of reverse micelles avoid limitations in sample size due to dielectric heating. In addition, the relatively slow motion of water in the hydration layer of encapsulated proteins renders polarization transfer to the protein efficient. For DNP in solution, the dynamics of the radical-water interaction may govern the strength of the polarization transfer via the Overhauser effect. Briefly, the enhancement is often expressed as:

$$\varepsilon = 1 - \zeta f s \left| \frac{\gamma_s}{\gamma_l} \right|,$$

where s is a saturation factor that describes the efficiency of saturation of the electron Zeeman transitions, f is a leakage factor that describes the paramagnetic enhancement of the nuclear relaxation rate over the total nuclear relaxation rate, and $\zeta$ is the coupling factor, which defines the magnetization transfer from the electron to the nuclear spin when the electron spin is saturated. The limiting factor among the three may be the coupling factor, because the saturation and leakage factors can be made close to one. The saturation factor may be optimized to approach 1 for even the large sample volumes for the reverse micelle system where application of sufficient GHz power is not an appreciable limitation.

The leakage factor may have a dependence on the exchange of magnetization of water hydrogens close to the spin label (bound waters) and the hydrogens in the rest of the water core. The leakage factor may be expressed as:

$$f = 1 - \frac{T_1}{T_{10}}$$

with $T_1$ describing the longitudinal relaxation time of the water hydrogens in the presence of the spin label and $T_{10}$, the longitudinal relaxation of the water hydrogens in the absence of the spin label. The water loadings typical for high-resolution protein NMR in reverse micelles ($W_0$=10-20) may result in an effective concentration of spin radical on the order of 50 to 100 mM. This may promote a higher contribution of paramagnetic relaxation to the total relaxation and thereby may tend to push the leakage factor to unity. As described herein, the reverse micelle system may offer the ability to optimize the relaxation characteristics through manipulation of the water loading and the number of spin probes provided.

For materials such as nitroxide radicals, which have no contact contribution to the DNP effect, the coupling factor $\zeta$(which is a measure of the motion of the electron and spin-bearing nuclear molecule relative to each other) may depend upon precise details of the motion modulating the interaction. Faster motion of water that may maximize the primary DNP effect may be counterbalanced by the slower motion of water that may enhance polarization transfer to the protein. As noted elsewhere in this disclosure, the nature of water dynamics within a reverse micelle can be manipulated to optimize the overall DNP process by, for example, (1) fine-tuning the reverse micelle sample, (2) scaling the ratio of magnetic field for the DNP, or (3) carrying out the SNP and the NMR in the same field or shuttling between a lower magnetic field for the DNP and a higher magnetic field for the NMR.

While enhanced nuclear spin polarization has been described in connection with the various embodiments of the various figures, it is to be understood that other similar embodiments may be used or modifications and additions may be made to the described embodiments for effectuating enhanced nuclear spin polarization without deviating therefrom. Therefore, enhanced nuclear spin polarization should not be limited to any single embodiment, but rather should be construed in breadth and scope in accordance with the appended claims.

What is claimed:

1. A method comprising:
hydrating a material;
encapsulating the hydrated material within a reverse micelle, the reverse micelle comprising a radical;
dissolving the reverse micelle in a low dielectric solvent adapted to avoid and/or mitigate dielectric loss;
exposing the reverse micelle to a magnetic field; and
concurrent with exposing the reverse micelle to the magnetic field, imparting energy from the radical to the material by applying electromagnetic radiation to the reverse micelle so as to enhance detection of characteristics of the material without causing catastrophic heating of the material.

2. The method of claim 1, wherein the radical has an electron spin.

3. The method of claim 1, wherein the material comprises a water-soluble molecule having a nuclear spin.

4. The method of claim 1, wherein the reverse micelle is shuttled from a first magnetic field to a second magnetic field.

5. The method of claim 1, wherein a second magnetic field having a field strength less than a field strength of the magnetic field is applied to the reverse micelle concurrent with imparting energy from the radical to the material by applying electromagnetic radiation to the reverse micelle.

6. The method of claim 1, wherein a frequency of the electromagnetic radiation is greater than 1 GHz.

7. The method of claim 1, wherein the reverse micelle increases a residence time of water on a surface of the encapsulated material.

8. The method of claim 1, wherein the material comprises a water soluble molecule.

9. The method of claim 3, wherein the water-soluble molecule comprises at least one of a protein, polysaccharide, polypeptide, or a polynucleotide.

10. The method of claim 2, wherein the radical is embedded in the reverse micelle.

11. The method of claim 2, wherein the radical is embedded in a surfactant layer of the reverse micelle.

12. The method of claim 2, wherein the radical is located in a water core of the reverse micelle.

13. The method of claim 2, wherein the radical is attached to the hydrated material.

14. A method comprising:
hydrating a material;
encapsulating the hydrated material within a reverse micelle, the reverse micelle comprising a radical;
dissolving the reverse micelle in a low dielectric solvent;
exposing the reverse micelle to a magnetic field; and
concurrent with exposing the reverse micelle to the magnetic field, imparting energy from the radical to the material by applying electromagnetic radiation to the reverse micelle,
wherein the reverse micelle comprises a surfactant mixture including 1-decanoyl-rac-glycerol (10MAG) and lauryldimethylamine-N-oxide (LDAO).

15. The method of claim 2, wherein the radical comprises a nitroxide radical.

* * * * *

UNITED STATES PATENT AND TRADEMARK OFFICE
CERTIFICATE OF CORRECTION

PATENT NO. : 9,778,335 B2
APPLICATION NO. : 14/400471
DATED : October 3, 2017
INVENTOR(S) : Andrew Joshua Wand Page 1 of 1

It is certified that error appears in the above-identified patent and that said Letters Patent is hereby corrected as shown below:

In the Specification

<u>Column 1</u>
Lines 16-19, delete "This invention was made with government support under Grant number MCB1158038 awarded by the National Science Foundation. The government has certain rights in the invention."

And insert:
--This invention was made with government support under Grant Number MCB1158038 awarded by the National Science Foundation and Grant Number GM107829 awarded by the National Institutes of Health. The government has certain rights in the invention.--

Signed and Sealed this
Thirtieth Day of July, 2019

Andrei Iancu
*Director of the United States Patent and Trademark Office*